(12) United States Patent
Narasimha-Iyer et al.

(10) Patent No.: US 10,149,610 B2
(45) Date of Patent: Dec. 11, 2018

(54) METHODS AND SYSTEMS FOR AUTOMATIC DETECTION AND CLASSIFICATION OF OCULAR INFLAMMATION

(71) Applicant: Carl Zeiss Meditec, Inc., Dublin, CA (US)

(72) Inventors: Harihar Narasimha-Iyer, Livermore, CA (US); Mary K. Durbin, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 521 days.

(21) Appl. No.: 14/688,753

(22) Filed: Apr. 16, 2015

(65) Prior Publication Data
US 2015/0305614 A1    Oct. 29, 2015

Related U.S. Application Data

(60) Provisional application No. 61/984,278, filed on Apr. 25, 2014, provisional application No. 62/092,782, filed on Dec. 16, 2014.

(51) Int. Cl.
*A61B 3/00* (2006.01)
*G06K 9/00* (2006.01)
(Continued)

(52) U.S. Cl.
CPC ........ *A61B 3/0025* (2013.01); *G06K 9/00617* (2013.01); *G06T 7/0012* (2013.01);
(Continued)

(58) Field of Classification Search
CPC .......... A61B 3/102; G06T 2207/10101; G06T 2207/30041
See application file for complete search history.

(56) References Cited

U.S. PATENT DOCUMENTS 5,114,973 A * 5/1992 Hess .............. A61K 31/19
514/557
6,095,648 A * 8/2000 Birngruber .......... A61B 3/1225
351/214
(Continued)

FOREIGN PATENT DOCUMENTS

WO    2010/117386 A1    10/2010
WO    2013/148687 A2    10/2013

OTHER PUBLICATIONS

Agarwal et al.: "High-Speed Optical Coherence Tomography for Imaging Anterior Chamber Inflammatory Reaction in Uveitis: Clinical Correlation and Grading", American Journal of Ophthalmology, vol. 147, No. 3, 2009, pp. 413-416.*
(Continued)

*Primary Examiner* — Gandhi Thirugnanam
(74) *Attorney, Agent, or Firm* — Morrison & Foerster LLP

(57) ABSTRACT

Systems and methods to improve the detection and classification of inflammation in the eye are presented. The inflammatory markers in image data can be graded by comparing identified and extracted characteristics from the images with characteristics derived from a set of images of eyes from a general population of subjects. The image data can be divided into sub-regions for analysis to better isolate the true inflammatory markers from the impacts of cataracts or other opacities. In another embodiment, the location of an imaging beam can be controlled to minimize the impact of lens opacities from the collected data used to analyze the inflammation state of an eye.

15 Claims, 6 Drawing Sheets

(51) Int. Cl.
*G06T 7/00* (2017.01)
*A61B 3/10* (2006.01)
*A61B 3/12* (2006.01)

(52) U.S. Cl.
CPC ................ *A61B 3/102* (2013.01); *A61B 3/12* (2013.01); *G06K 2209/05* (2013.01); *G06T 2207/10101* (2013.01); *G06T 2207/30041* (2013.01); *G06T 2207/30242* (2013.01)

(56) References Cited

U.S. PATENT DOCUMENTS

| | | | | |
|---|---|---|---|---|
| 6,254,860 | B1* | 7/2001 | Garst | A61K 38/13 424/78.04 |
| 7,301,644 | B2* | 11/2007 | Knighton | A61B 3/102 356/479 |
| 7,805,009 | B2* | 9/2010 | Everett | A61B 3/102 382/128 |
| 8,348,429 | B2 | 1/2013 | Walsh et al. | |
| 8,632,180 | B2* | 1/2014 | Narasimha-Iyer | A61B 3/102 351/206 |
| 2003/0179948 | A1* | 9/2003 | Gindele | G06T 5/007 382/274 |
| 2003/0223038 | A1* | 12/2003 | Alster | A61B 3/02 351/211 |
| 2007/0291277 | A1* | 12/2007 | Everett | A61B 3/102 356/497 |
| 2009/0244485 | A1* | 10/2009 | Walsh | A61B 3/1005 351/221 |
| 2012/0020539 | A1* | 1/2012 | Derr | G06K 9/4652 382/131 |
| 2012/0075584 | A1* | 3/2012 | Stetson | A61B 5/0059 351/206 |
| 2012/0249956 | A1* | 10/2012 | Narasimha-Iyer | A61B 3/102 351/206 |
| 2012/0274897 | A1* | 11/2012 | Narasimha-Iyer | A61B 3/102 351/206 |
| 2012/0274900 | A1* | 11/2012 | Horn | A61B 3/102 351/206 |
| 2012/0321719 | A1* | 12/2012 | McDonnell | A61K 9/0051 424/497 |
| 2013/0100404 | A1* | 4/2013 | Narasimha-Iyer | A61B 3/102 351/206 |
| 2013/0162946 | A1* | 6/2013 | Dobashi | A61B 3/14 351/206 |
| 2014/0276025 | A1* | 9/2014 | Durbin | A61B 5/4842 600/427 |
| 2015/0062590 | A1* | 3/2015 | Bagherinia | G01B 9/02091 356/479 |
| 2015/0305614 | A1* | 10/2015 | Narasimha-Iyer | G06T 7/0012 351/206 |

OTHER PUBLICATIONS

International Preliminary Report on Patentability received for PCT Patent Application No. PCT/EP2012/057416, dated Nov. 7, 2013, 9 pages.
International Search Report and Written Opinion received for PCT Patent Application No. PCT/EP2012/057416, dated Sep. 7, 2012, 14 pages.
Non Final Office Action received for U.S. Appl. No. 13/449,227, dated Jun. 19, 2013, 11 pages.
Notice of Allowance received for U.S. Patent Application No. 13/449,227, dated Sep. 17, 2013, 8 pages.
Non-Final Office Action received for U.S. Appl. No. 14/156,199, dated Oct. 10, 2014, 9 pages.
Notice of Allowance received for U.S. Appl. No. 14/156,199, dated Feb. 17, 2015, 8 pages.
Abramoff et al., "Retinal Imaging and Image Analysis", IEEE Reviews in Biomedical Engineering, vol. 3, 2010, pp. 169-208.
Agarwal et al., "High-Speed Optical Coherence Tomography for Imaging Anterior Chamber Inflammatory Reaction in Uveitis: Clinical Correlation and Grading", American Journal of Ophthalmology, vol. 147, No. 3, Mar. 2009, pp. 413-416.
Agarwal et al., "Using OCT to Assess Anterior Chamber Inflammation", Ophthalmology Times Europe, vol. 4, No. 2, Mar. 2008, pp. 1-4.
Al et al., "A Magnitude-Based ART2 Classifier: Structure and Algorithms", IEEE, Proceedings of the 6th World Congress on Intelligent Control and Automation, vol. 2, Jun. 21-23, 2006, pp. 9799-9803.
Davis et al., "PA073 Vitreous Haze Grading: An Analysis of Outcomes in the Multicenter Uveitis Steroid Treatment Trial (MUST)", Nov. 12, 2012, 1 page.
Davis et al., "Scale for Photographic Grading of Vitreous Haze in Uveitis", American Journal of Ophthalmology, vol. 150, No. 5, Nov. 2010, pp. 637-641.
Huang et al., "Optical Coherence Tomography", Science, vol. 254, No. 5035, Nov. 22, 1991, pp. 1178-1181.
Kim, Stephen J., "The Role of Imaging in the Diagnosis and Management of Uveitis", Expert Review of Ophthalmology, vol. 5, No. 5, Oct. 2010, pp. 699-713.
Lee et al., "In vivo Optical Frequency Domain Imaging of Human Retina and Choroid", Optics Express, vol. 14, No. 10, May 15, 2006, pp. 4403-4411.
Leitgeb et al., "Ultrahigh Resolution Fourier Domain Optical Coherence Tomography", Optics Express, vol. 12, No. 10, May 17, 2004, pp. 2156-2165.
Li et al., "Anterior Chamber Cell Grading by Optical Coherence Tomography", Multidisciplinary Ophthalmic Imaging, IOVS, vol. 54, No. 1, Jan. 2013, pp. 258-265.
Lowder et al., "Anterior Chamber CeU Grading with High-Speed Optical Coherence Tomography", Investigative Ophthalmology and Visual Science, vol. 45, No. 5, 2004, 2 pages.
Madow et al., "Validation of a Photographic Vitreous Haze Grading Technique for Clinical Trials in Uveitis", American Journal of Ophthalmology, vol. 152, No. 2, Aug. 2011, pp. 170-176.
Onal et al., "Optical Coherence Tomography Imaging in Uveitis", International Ophthalmology, vol. 34, No. 2, Jul. 2013, pp. 401-435.
Wojtkowski et al., "Three-dimensional Retinal Imaging with High-Speed Ultrahigh-Resolution Optical Coherence Tomography", Ophthalmology, vol. 112, No. 10, Oct. 2005, pp. 1734-1746.

* cited by examiner

METHODS AND SYSTEMS FOR AUTOMATIC DETECTION AND CLASSIFICATION OF OCULAR INFLAMMATION

PRIORITY

The present application claims priority to U.S. Provisional Application Ser. No. 61/984,278 filed Apr. 25, 2014 and U.S. Provisional Application Ser. No. 62/092,782 filed Dec. 16, 2014, the contents of both of which are hereby incorporated by reference.

TECHNICAL FIELD

The present application is directed towards improved detection and classification of ophthalmic inflammation, in particular inflammation characteristic of uveitis.

BACKGROUND

Inflammation in the eye often causes the appearance of cells, flare and haze in the anterior and posterior chambers of the eye. A common inflammation is uveitis, which is frequently associated with swelling and inflammation of the uvea, the middle layer of the eye. The uvea consists collectively of the iris, the choroid, and the ciliary body. Uveitis can exist in the front of the eye (anterior uveitis or iritis, hereinafter UV-A), the middle region of the eye (intermediate uveitis, including pars planitis, hereinafter UV-I), the back of the eye (posterior uveitis, hereinafter UV-P), or throughout the eye (panuveitis or diffuse uveitis). The cells present in uveitis are white blood cells that are visible inside the eye. Flare and haze are measures of protein and inflammatory debris within the eye that can appear in active uveitis. Flare is typically associated with anterior uveitis and haze with intermediate and posterior uveitis. Haze/flare is used herein to refer generally to this indicator of inflammation. Manual slit-lamp examination has been the standard method for assessment of the inflammatory reaction in case of uveitis. A variety of classification schemes have been developed and applied to uveitis.

The most common form of uveitis is UV-A, which involves inflammation in the front part of the eye, usually the iris. UV-A can be divided into acute and chronic types based on the duration of the inflammation. A further classification is granulomatous and non-granulomatous. Granulomatous uveitis typically presents with large, greasy precipitates on the corneal endothelium with large clumps of inflammatory cells present in the anterior chamber because of exuberant macrophage activity. Nongranulomatous uveitis typically presents with fine cornea endothelial precipitates and anterior chamber activity (clumps).

A grade or marker for the severity of uveitis can be derived from the number of cells or clumps present in the aqueous humor according to the 2005 Standardization of Uveitis Nomenclature (SUN), which is based upon criteria as defined by the International Uveitis Study Group. This grading system typically uses the information derived from visual inspection using a 1 mm by 3 mm slit beam. For anterior segment cell counts, grade 0 means no cells found and a grade of 4 implies a cell count in excess of 50. Additional classification and grading schemes can include the cell count data as well as factors including the level, origin, location of inflammation, and the amount of haze and/or flare present in different regions of the eye (see, e.g., Madow et al. 2011). These schemes rely heavily on manual examination and interpretation of data. Clinical assessment is subjective and often difficult in eyes with corneal or cataractic opacification from non-uveitic sources.

Optical Coherence Tomography is a non-invasive, in-vivo imaging technique based on the back-scatter or reflectivity of light in a medium (see, e.g., Huang et al. 1991). In ophthalmic examinations, the beam of light produced by the OCT device scans the eye through the pupil and the image formation process records the back-scattering profile of the light at each location. The amount of scatter is indicative of the reflectivity of the tissue encountered, and a grayscale cross-sectional image is formed as the light beam sweeps across the field of view (FOV). OCT imaging has dramatically advanced ophthalmic diagnostic capabilities and led also to better understanding of ocular anatomy. It is now an established basis of routine ophthalmic practice. Several implementations of OCT have been developed including time domain (TD-OCT) and frequency domain (FD-OCT) which covers both spectral domain (SD-OCT) and swept-source (SS-OCT).

The clumps of inflammatory cells present in the anterior chamber of patients with uveitis appear as bright or hyper-reflective spots in OCT images. Thus counting hyper-reflective spots in OCT images can be used to grade uveitis. Methods have been described to determine or assess the risk of uveitis based on intensity levels of the image signal as compared to a database of normal and abnormal values. Agarwal et al. (2009) compared manual and automated counting of the hyper-reflective spots in OCT images of the hyper-reflective spots in anterior chamber. An automated method for identifying, quantifying and classifying cell clumps visible in OCT images is described in U.S. Pat. No. 8,632,180.

Inflammation in the vitreous, as in the anterior chamber, is characterized by increased cells and protein. This increases the level of haze/flare present in the eye. The vitreous is rarely the source of the inflammatory cells; the inflammatory cells arise instead from the choroid, retina, and ciliary body. The cells that form the haze/flare can also be from the breakdown of the blood-ocular barrier. However, in certain infections the focus of the inflammation may be in the vitreous. Both vitreous cells and haze/flare are more difficult to quantify than aqueous cells and haze/flare.

Vitreous haze/flare can be observed in images of the retina and anterior haze/flare could be observed in images of the anterior eye. It is currently the practice to grade vitreous haze/flare by manually comparing the subject's fundus image to "standard" fundus images with the different grades of haze/flare. FIG. 1 shows such a set of standard fundus images with different haze/flare grades (Davis 2012). The grading criteria for the images was: if the nerve fiber layer (NFL) is clearly visible, a grade of 0; if the optic disc or optic nerve head (ONH) and vessels are clear but the visibility of the NFL is hazy, then a grade of 1; for hazy ONH and vessels, a grade of 2; for only ONH visible, the grade of 3; and finally if the ONH is not visible, then a grade of 4. While standard fundus photography was used to collect the images of FIG. 1, various modalities of fundus imaging include SLO (scanning laser ophthalmoscope), cSLO (confocal SLO), LSO (line scanning ophthalmoscope, and BLFI (broad line fundus imager) are capable of producing comparable images for grading of haze/flare.

Posterior uveitis is associated with the highest risk of severe vision loss, and is an inflammation associated with the posterior segment of the eye. The condition can be further characterized based upon whether the retina or the choroid is the predominant site of inflammation. In more severe cases of UV-P, UV-A (cells and flare) is also likely to be present. UV-P inflammation can frequently result in alterations of tissues or layers, such as those in the retina; these often appear as generalized increases in thickness, or local irregularities in the thickness of a layer of interest. Alternately, UV-P can appear as local areas of hyper-reflectivity or hypo-reflectivity within specific layers or tissues.

The evaluation of haze/flare in fundus images is complicated by media opacities that can affect the perception of uveitic haze/flare. The most important degradation is due to the presence of cataracts, a source that can mimic uveitic haze/flare. Separating the effect of such degradations will yield better diagnoses of the etiology of uveitis.

Fundus imaging represents a 2D projection of a 3D system (the eye: anterior, lens, posterior) so provides limited information as to the precise location of the inflammation. OCT provides depth information so can be a useful technique to apply to analyzing the haze/flare in inflamed eyes. A further advantage of the use of OCT for the current application is that infrared light that is used as a probing beam of tissues may have greater penetration through the sites of inflammation, such as haze/flare, than possible with the visual light used in manual examinations.

Proper treatment of inflammation and its efficacy will depend upon accurate and consistent grading of the true inflammation. Subjective or manual grading can add uncertainty in the treatment standards. Thus a methodology that removes some of the uncertainty in the grading should improve the clinical management of uveitis as well as the ability to develop and test effective therapies more efficiently.

SUMMARY

The present application describes methods and systems to improve the detection and classification of inflammation in the eye. In one embodiment, fundus images containing haze and/or flare are automatically graded or classified by comparing identified and extracted characteristics from the images with characteristics derived from a set of images of eyes from a general population of subjects. The classifier used for this task could be created using a supervised or unsupervised algorithm. In addition to standard fundus images, characteristic metrics related to haze/flare can be extracted from optical coherence tomography (OCT) image data. Haze/flare information can be combined with automatic detection of inflammatory cells or clumps in OCT image data to provide an overall classification or grade of the inflammation using any one of a number of classification schemes. A classifier could also be created using the OCT data or OCT data in combination with the fundus data, again using supervised or unsupervised learning on a dataset that included eyes with and without uveitis.

Further embodiments take advantage of the depth resolved imaging capability of OCT to discern the locations of the cells and the location and nature of uveitic haze/flare and opacities within the eye in order to improve the accuracy of the grading of uveitis. As the anterior chamber is not affected by the opacity of the crystalline lens, separate and or joint analysis of the image data from the anterior and posterior chamber allows removal of the effect of the lens opacity from the computation of the haze/flare grade. In one embodiment, once the level of opacity has been determined from OCT data, the grade of haze/flare previously obtained from fundus images can be adjusted to a more realistic value. An OCT instrument can be configured to obtain and process images, yielding a grade and type or types of uveitis.

Another embodiment involves using pupil tracking to optimize and maintain the location on the pupil where OCT image data is collected thereby minimizing the impact of any lens opacity on the collected data in the first place.

In another embodiment, unsupervised clustering of the detected clumps as well as location information are used to classify the clumps into different types. The location of the clumps can also be used to augment their classification. For example, in the anterior chamber, a particular type of clump might be found closer to the cornea or even touching it. The location information can then be used to strengthen the identification and thus the classification of the clumps.

DETAILED DESCRIPTION

Figure 1:
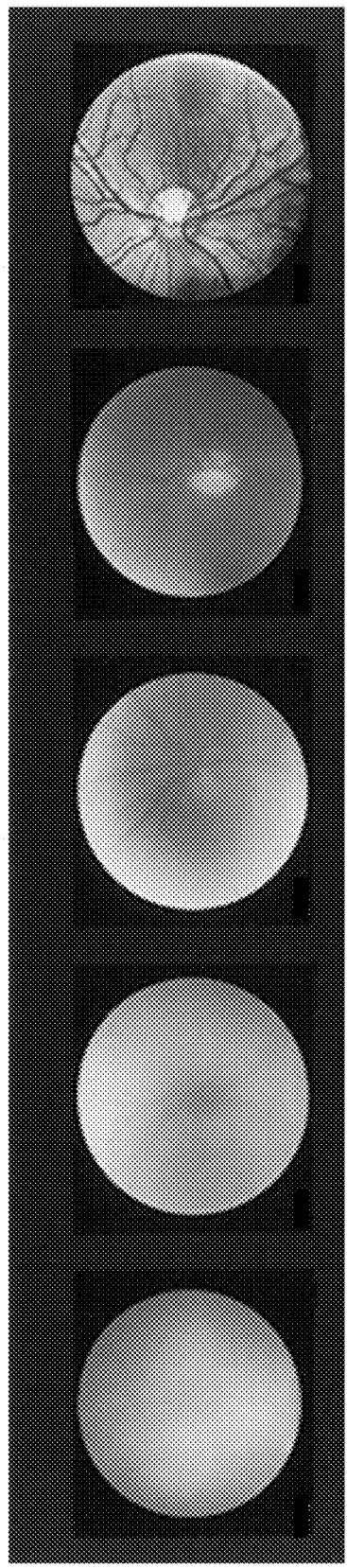
FIG. 1 shows a series of fundus images with varying amounts of haze/flare.
Figure 2:
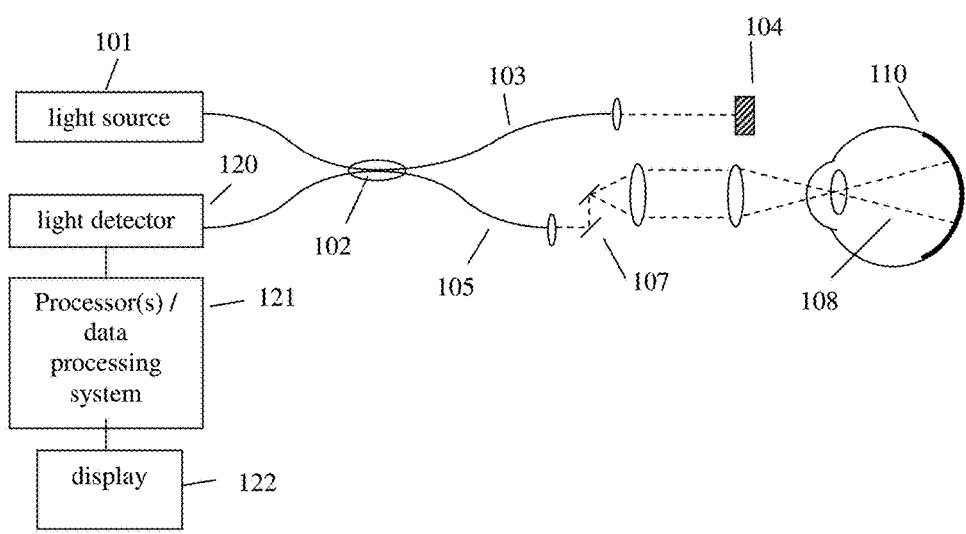
FIG. 2 is a diagram of a basic frequency-domain optical coherence tomography (FD-OCT) system.

A diagram of a generalized frequency-domain OCT (FD-OCT) system for use in ophthalmology is shown in FIG. 2. Light from source 101 is routed, typically by optical fiber 105, to illuminate the sample 110, a typical sample being tissue in the human eye. Typical sources are a broadband light source with short temporal coherence length in the case of spectral-domain OCT (SD-OCT), or a wavelength-tunable laser source in the case of swept-source OCT (SS-OCT). The beam of light (dashed line 108) is scanned laterally or transversely (in x and y, if z is parallel to the beam of light) over the area or volume to be imaged, typically with scanning optics 107 between the output of the fiber and the sample. In the case of retinal imaging, light is scanned over the retina of the eye while maintaining the same entry location on the pupil. Light back-reflected from the sample returns through scanning optics 107 and is collected, typically into the same fiber 105 used to route the light for sample illumination. Lens 109 is used to collimate the illuminating light exiting the fiber and to focus the reflected light back into the fiber for collection. Reference light derived from the same source 101 travels a separate path, in this case involving fiber 103 and retro-reflector 104 with an adjustable optical delay. Those skilled in the art will recognize that a transmissive reference path can also be used and that the adjustable delay could be placed in either the sample or reference arm of the interferometer. Additionally, the interferometer could consist of fiber optics, bulk optical components, or a combination thereof. Collected sample light is combined with reference light, typically in a fiber coupler 102, to form light interference in a detector 120, which generates output signals. Although a single fiber port is shown going to the detector, those skilled in the art will recognize that various designs of interferometers can be used for balanced or unbalanced detection of the interference signal. The output from the detector is supplied to a processor or processors 121. The results can be stored in the one or more processors 121 or displayed on display 122. Alternatively, the information can be conveyed by reporting to a user as can any subsequent measurements derived from data obtained with an OCT system. A data processing system may consist of one or more processors, not necessarily located in close proximity to one another, and associated peripherals such as displays.

The processing and storing functions may be localized within the OCT data collection instrument and/or other functions may be performed on an external processing system to which the collected data is transferred. This could be dedicated to data processing or perform other tasks that are quite general and not dedicated to the OCT imaging device. One or more of the processors can be of the parallel processing type such as GPUs, FPGAs, or multi-core processors. As FIG. 2 is a generalized OCT instrument, typical instruments are normally configured to image the retina. To image the anterior segment, additional lenses are usually inserted into the instrument to focus the beam in the anterior chamber.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample. The scattering profile as a function of depth is called an axial scan (A-scan). A set of A-scans measured at neighboring locations in the sample produces a cross-sectional image (tomogram or B-scan) of the sample. A collection of B-scans makes up a data cube or volume or volumetric image. It should be noted, however, that the application of these methods need not be limited to data acquired via FD-OCT; they could also be applied to data acquired via other OCT variants including TD-OCT, multi-beam OCT, and parallel OCT configurations. The methods of the present invention can be applied to OCT data collected using systems designed to reduce the complex conjugate artifact to further reduce the impact of artifacts on the collected data.

Figure 3:
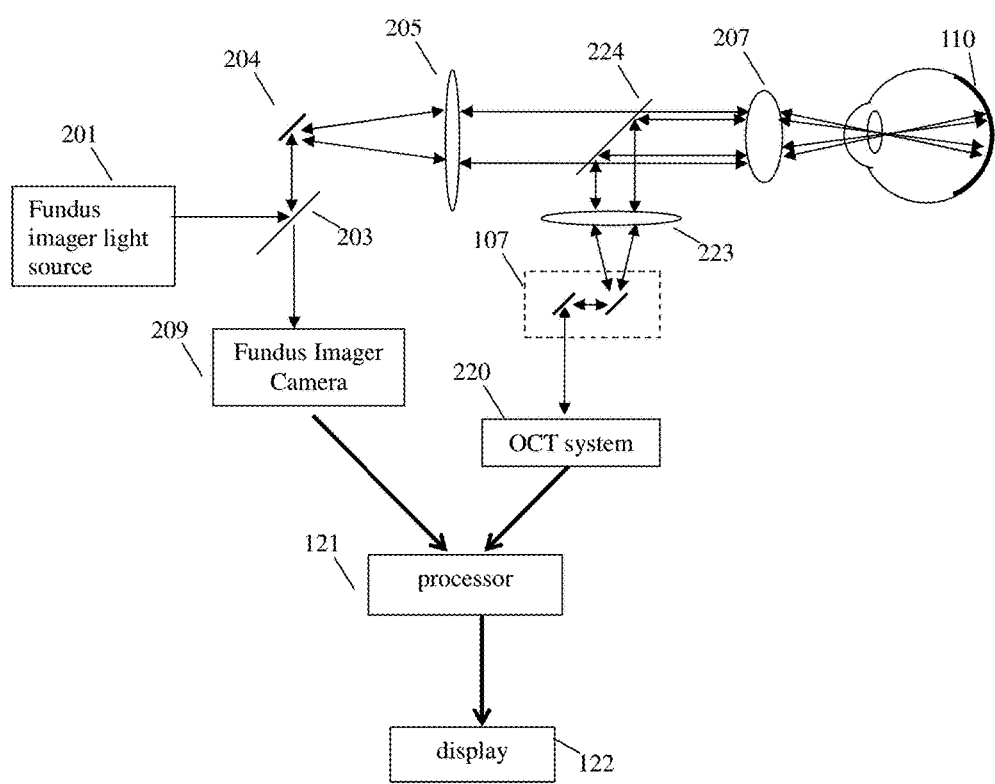
FIG. 3 illustrates a combined OCT and fundus imaging system.

An OCT imaging system can easily be combined with a fundus imaging modality as illustrated in FIG. 3. Here fundus imager light source 201 is reflected off of mirrors 203 and 204, and passes through lenses 205 and 207 on the way to the eye 110. The system is generalized and could comprise any type of fundus imaging including, but not limited to, traditional fundus photography, spot, line, or slit scanning ophthalmoscopy. In the case of a scanning modality, one or both of mirrors 203 and 204 would have scanning functionality. The fundus imaging light returning from the retina travels along the same path passing through mirror 203 on the way to the camera 209. OCT system 220 includes the light source, detector and most of the interferometer described in reference to FIG. 2. A portion of the sample arm is displayed in FIG. 3. After reflecting off scanning elements 107 and passing through lens 223, the light is reflected off of mirror 224 on its way to the eye 110. The OCT and fundus imaging light paths are separated at beam splitting element 224. The detected light for both systems can be processed in processor 121 and displayed on display 122. The data from one modality can be used to guide the acquisition or analysis of the other modality (see for example U.S. Pat. No. 7,805,009, US Patent Publication No. 2012/0249956, US Patent Publication No. 2014/0276025).

Figure 4:
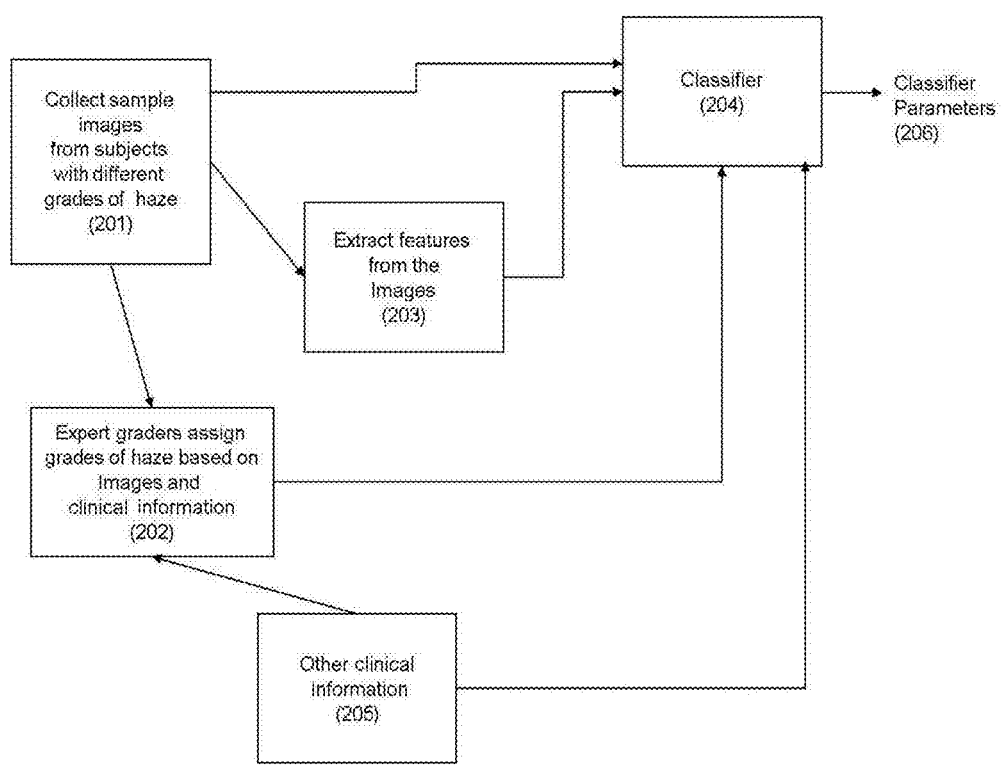
FIG. 4 is a flow chart showing the steps involved with training a classifier for haze/flare evaluation.
Figure 5:
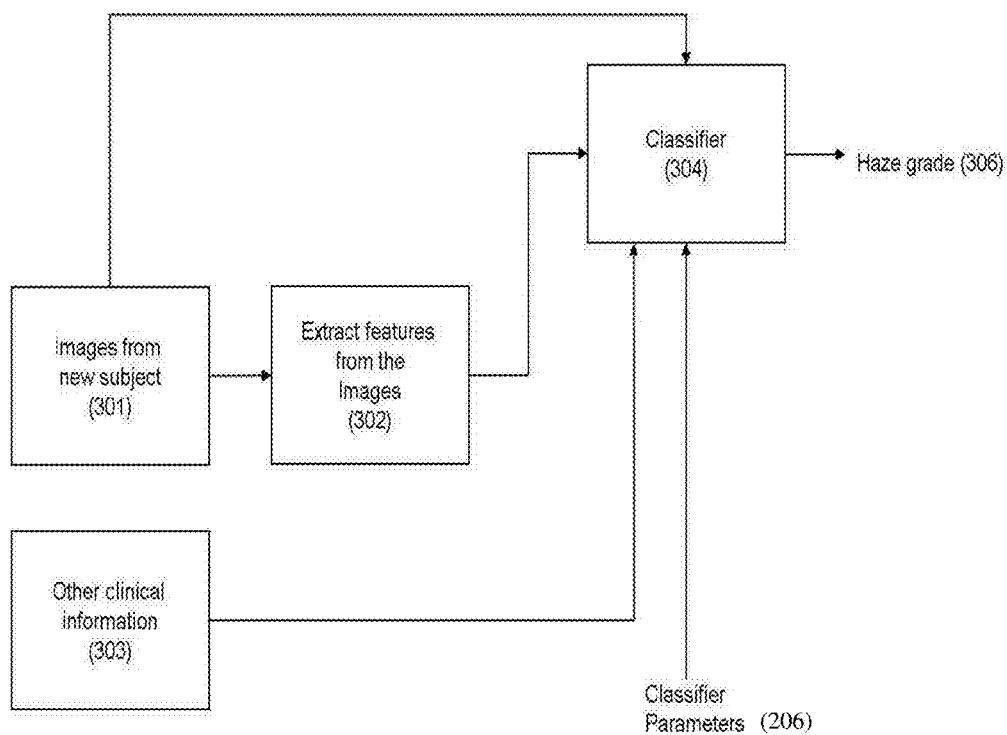
FIG. 5 is a flow chart illustrating the steps involved with an automated determination of haze/flare.

In one embodiment of the present application illustrated in FIGS. 4 and 5, data from an image data set is automatically analyzed to assess the level of haze and/or flare in the image. This involves two parts: training of the classifier and grading of the individual data set. FIG. 4 is a flow chart demonstrating the development of classifier parameters for use in grading vitreous haze. In the first step of the process, a set of training data from a population of subjects with different grades of haze is collected (201). Images could be fundus images, OCT images, or a combination of both. It is recommended that the images be centered on anatomical structures such as the optic disc (aka optic nerve head or ONH) since this will provide the maximum structure information near the center of the image. OCT images from the anterior and posterior parts of the eye can also be collected. For OCT images, the preferred scan pattern would be a cube scan pattern with sufficient lateral and axial resolution to detect hyper-reflective clumps if present. Cube scan patterns are preferred for both posterior and anterior imaging of the eye using OCT.

In a multimodal system with fundus imaging and OCT, the different images could be obtained either simultaneously or sequentially. Other clinically relevant information can also be collected from each subject (205). Examples of such information include age/prior medical history including illnesses/trauma/-symptoms, visual acuity etc. While most cases of uveitis are idiopathic, a history focused on identifying a potential underlying systemic cause (e.g., in young adult men, conjunctivitis, urethritis, and polyarthritis suggest reactive arthritis) could provide other characteristics that could be parameterized and included in the classifier. Once all this information is available, clinicians would be asked to record a haze grade to the subject after looking at the collection of images, other available relevant information as well as information from a clinical examination (202). If anterior and posterior images are available, the clinician would record a haze grade separately for the anterior and posterior chambers.

The collected and graded images are then processed to identify and extract characteristics (203). Eyes beset with haze suffer a loss of contrast and as a result anatomical structures become lost or their outlines diminished. Characteristic metrics that can be extracted from the images include intensity, mean gradient, peak gradient, mean/median gradient, intensity moments, contrast measures within a block or region, texture parameters, shape parameters, geometric parameters, standard deviation of brightness or intensity values, and canonical statistical measures such as mean, mode, median, variances, moments, and the like. As will be described in further detail below, these metrics can be determined on different portions of the image to isolate the inflammation to specific locations or remove or reduce the impact of media opacities.

Once the aforementioned morphological characteristics have been extracted (203), these can be used, along with other relevant information (205), as well as the haze and flare grades assigned by the clinicians (202), to train a machine learning classifier (204) to "learn" how haze and flare grades can be assigned to the subjects. Many different classifiers have been described in the literature. Classifiers such as k-Nearest Neighbor (k-NN), Support Vector Machines (SVM), Artificial Neural Networks (ANN), Random Forests, clustering as a mixture of Gaussians, hierarchical, and other options could be used for the embodiments of the current application (see, e.g., Kaufman & Rousseeuw 2005). These are just examples and those skilled in the art could use any type of classifier. In this application, the output classes are haze/flare grades from 0 (No Haze) to 4 (significant haze). The output of the classifier training stage (206) is a set of parameters that define the decision boundaries given the characteristics sets. These parameters (206) could then be saved in the system for future use. Should the system of grading ocular inflammation change, then naturally re-calibration of the classifier will be required, and would not affect the embodiments of the present application. In another embodiment, the training could be done using an unsupervised algorithm, such as principal components analysis or clustering could be used to identify eyes that contain different haze/flare levels. A classification scheme developed by such an algorithm, independently of clinician grading, could potentially support creating a finer grading scale or one that is more clinically useful. Subsequent testing could identify the correlation between the old scheme and the proposed new scheme.

Reference is now made to FIG. 5 which shows how the classifier parameters can be applied to an individual subject to grade the haze/flare. For a new subject whose haze grade has to be determined, the required image data are first collected (301) along with other relevant clinical information (303). The characteristics as described previously are extracted and processed (302) and then input to the classifier (304). The classifier then outputs a haze grade (306) based on the input characteristics and the stored parameters (305) from the training. This grade can be then displayed to the user using an User Interface, stored in the database along with the images as well as tracked over time to monitor progression of disease and the efficacy of treatments.

U.S. Pat. No. 8,632,180 describes how OCT can be used to automatically identify, quantify and classify cell clumps in OCT images of the eye. The cell clump data derived from that technique could be used as a further input to a classification system for providing a more complete analysis and classification of the inflammation.

The ability to understand properly the origin of uveitic haze/flare in ocular tissue is dependent upon successful separation of that type of haze/flare from other sources of opacity. One predominant source for signal reduction is that from cataracts in the crystalline lens of the eye. This type of opacity can mask, hide, or mimic uveitic conditions in the post-lens conditions (UV-I or UV-P).

Figure 6:
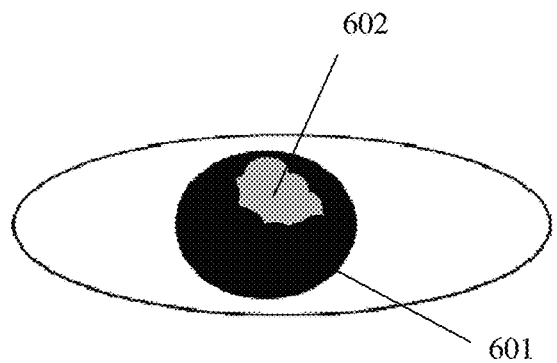
FIG. 6 illustrates a cataract opacity projected onto the pupil of an eye.

FIG. 6 illustrates a cataract opacity 602 projected onto the pupil 601 of an eye that would cause signal degradation when imaged through that opacity. Here uveitic haze/flare is present in the vitreous in addition to the opacity in the crystalline lens, but the haze/flare in this case is not visible as it would be behind the crystalline lens. In order to grade the level of haze/flare more accurately, the signal degradation caused by the cataractic opacity needs to be estimated, and removed or taken into account in the classification of the uveitic haze/flare. One way this can be accomplished is by incorporating any cataractic opacity as one of the inputs to a uveitis classifier.

OCT imaging, unlike fundus imaging, has the ability to provide depth as well as transverse information. As different types of uveitis originate from different anatomical regions and have different inflammatory signatures, OCT images of the anterior and the posterior chambers of the eye, as well as that of the crystalline lens (which separates the two chambers) can be obtained either simultaneously or sequentially and analyzed to reveal the nature and location of cells, haze/flare and/or opacities located therein. This makes it possible to isolate the signatures of inflammation based on their location. For instance, obtaining A-scans of the anterior chamber, OCT images before the crystalline lens would aid in estimating the degree of haze/flare in the anterior chamber. If the source and level of opacity in an eye of a patient is determined, a pre-existing grade for that eye can then be adjusted. The pre-existing grade may have been derived from a fundus imaging modality.

In one embodiment of location dependent inflammation analysis, OCT image data is sub-divided into a number of blocks (i.e., subimages) and then characteristics related to uveitis are computed within a block. A block can possess a one, two, or three-dimensional structure. A given block could be located exclusively within any anatomical entity, such as the cornea, the aqueous humor (anterior chamber), the crystalline lens, the vitreous humor (posterior chamber), or the retina. There could be multiple blocks defined within each of these anatomical entities, and along any dimension or projection, such as, for example, the longitudinal axis. Each of these blocks can be processed or analyzed to discern the number of cells, the extent and location of opacities, and the extent or level of haze/flare contained therein. Such a block might be specific to an anatomical region such as the anterior chamber, the posterior chamber, the crystalline lens, or the retina.

The rationale behind dividing the images into blocks (or subimages) is that in typical images of the eye, anatomical structures are usually concentrated in some regions with less structure towards the periphery. Dividing the image into blocks would allow one to capture this natural variation in the appearance of the image at different locations. It can also aid in identifying the origin or location of any source of opacity. The source of the opacity can be identified based upon which region the OCT data were obtained from, e.g., anterior segment, or in the vitreous humor. Also this block-based approach would help to identify the location of the inflammation along the lateral dimensions in the image.

Morphological, structural, and positional characteristic metrics that can be derived from analyses of these sub-images can then be used in the classification of uveitis, preferably through an automated classification system as previously described. Useful characteristic metrics can include, but are not limited to, signal strength, opacity, reflectivity, intensity or texture within a given area or layer compared to background, presence of cells/clumps in the aqueous/-vitreous, counts of such cells, retinal or corneal thickness information, or the presence of hyper-reflective inflammatory processes within specific layers of the retina.

In another embodiment, there is the ability to segment the various layers in the retina such as inner limiting membrane (ILM), retinal nerve fiber layer (RNFL or NFL), and retinal pigment epithelium (RPE) and to determine characteristics from each of the layers separately. However, since disease affects the interior of the retina as well, characteristics calculated separately from the interior of the retina could also help in identifying the disease state. In the case of UV-P, it has been noted that the presence of this disease is correlated with the thickness of retinal tissues or layers. One characteristic derivable from multi-layer segmentation of OCT images is the thickness (or thicknesses) of one or more anatomical or retinal layers.

Anatomical sections defined by segmentations can be segregated into slabs or enface images: regions of interest generated by summing or otherwise combining voxels in a preferred projection (see for example U.S. Pat. No. 7,301, 644). For example, from an OCT image of the posterior eye, we could create an enface image of just the vitreous portion above the ILM to enhance the detection of the clumps in that region. Other retinal regions of interest that could be identified from segmentation approaches are anatomical structures such as optic nerve head, blood vessels, and the fovea. For an anterior chamber OCT image, segmentations of structures such as the anterior and posterior cornea, iris and the anterior and posterior part of the lens might be obtained.

OCT scans can be analyzed in order to derive characteristic metrics related to levels of contrast found within the eye due to the increased scattering from uveitic products (cells, flare/haze, etc.). A metric which correlates with the amount of contrast found between the retinal layers and would be affected by the amount of haze/flare present (due to light scattering) is called segmentability and is described in US Patent Publication No. 2015/0062590. A segmentability map or metric can be determined and this information input to the grading of the uveitic haze/flare to aid in the accurate classification of that haze/flare. A segmentability metric or map is considered to be one of the characteristics that can be used to identify the location, and quantify a source of opacity. A segmentability metric can be derived along the longitudinal axis or laterally, or even volumetrically, or within the context of the block-based approach described above. Such a metric along the longitudinal axis would clearly separate opacities from those found in the anterior chamber, the crystalline lens, and the posterior chamber.

Another embodiment of the present application is the realization and identification that different types of cell clumps will have different relative distributions of their properties in general. U.S. Pat. No. 8,632,180 describes a technique to identify, quantify, and classify cellular clumps caused by inflammation based on their intensity and geometrical properties. New enhancements to this technique are now presented.

In one embodiment, morphological characteristics based on intensity and geometric characteristics are extracted from each clump identified in an OCT image. Some example characteristics for each detected clump could be mean intensity, max intensity, area of the clump, geometrical moments, eccentricity, volume, and shape. This is not an exhaustive list of characteristics and those skilled in the art can determine others with high sensitivity to distinguish between cell types. A collection of these characteristics from eyes of a population of subjects are used in an unsupervised clustering framework to "group" clumps that are similar in nature. (Cluster analysis is a branch of statistics that deals with the partitioning of multivariate data into subsets (or clusters), so that the data of each subset ideally share some common properties or traits. For a general introduction to cluster analysis, see Kaufman and Rousseuw 2005.) This would allow one to calculate the distribution of the different types of clumps. This distribution information is used during the classification of an individual eye to determine the cell type.

In another embodiment, the location of the clumps as can be determined by the methods previously described in this application is also used to classify them. For example in the anterior chamber, a particular type of clump might usually be found closer to the cornea/touching the cornea. The location information can thus be used to make the identification and classification more robust.

In general, in another aspect, the invention can be embodied in an apparatus for categorizing, among a set of user-specified categories, morphological characteristics which appear in an image based on visual and/or geometric properties of the spots or clumps. The apparatus includes an unsupervised classifier or unsupervised classification processor adapted to define clusters and to categorize these clusters based on morphological characteristics, and a supervised classifier or supervised classification processor adapted to map the clusters to the set of user-specified categories. In an embodiment, the unsupervised classifier can be an ART2 classifier (see, e.g., Ai et al. 2006).

In general, in another aspect, an apparatus includes a locator which determines the location of the spots or clumps within an image based on the intensity values and a classification processor which categorizes the morphological characteristics.

Once the ensemble of clumps have been identified, located, and their morphological characteristics computed, then the information derived therefrom, either in total or segregated according to location or morphological characteristics, may be combined into such statistical measures as mean, mode, and median, variance of the distributions obtained.

Typically OCT measurements are made by directing the measurement beam through the center of the pupil as described in US Patent Publication No. 2007/0291277. Often cataracts occur in the nucleus of the crystalline lens. An aspect of the present application is to use the fact that different pupil entry positions give different measurement signals and hence it will be possible to find an optimal pupil entry position that minimizes the contribution of any haze/flare or media opacity that would be present in the crystalline lens and not due to the haze/flare due to inflammation. The general technique for finding and maintaining an optimum pupil entry position is described in US Patent Publication No. 2012/0274897. The process can be carried out automatically within an ophthalmic diagnostic system comprising an optical coherence tomography system, one or more processors, and a controller as described in further detail below.

Figure 7:
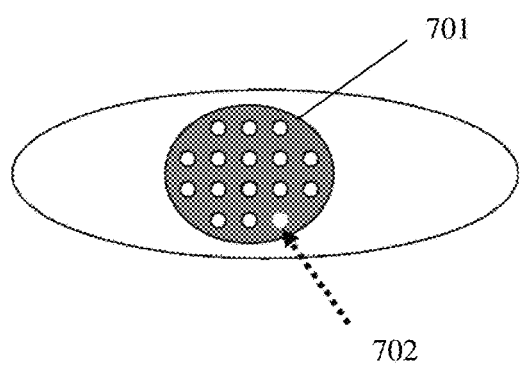
FIG. 7 shows a scanning arrangement that could be used to identify the optimal pupil entry location.

FIG. 7 illustrates a scanning pattern in which the pupil 701 is imaged or sampled in a grid pattern to roughly map out the observed opacities in the crystalline lens. Item 702 could be a preferred entry point. The figure shows a uniform grid of pupil entry locations of lateral (x and y) that extend across the pupil. Each of these pupil entry locations can be denoted as $PE_i$, where i corresponds to the index of the location. For each of the pupil entry locations, we can also record the resulting measurement signal, denoted as $M_i$, a typical measurement being an OCT A-scan. A correlation between the entry positions and the measurements can be maintained using a camera to collect images of the location of the measurement beam visible on the iris of the eye.

Figure 8:
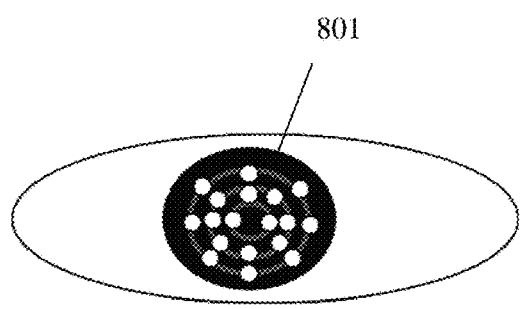
FIG. 8 shows an alternative scanning grid.

It is not necessary that the sampling pattern used be a uniform grid. Another possibility is shown in FIG. 8, with a series of measurements taken along concentric ring scanning patterns within the pupil 801. It should be noted that FIGS. 7 and 8 display only representative scan patterns and the invention is applicable to any sampling pattern.

The optimal pupil entry location can be determined by a processor by defining an optimality condition on the measurement signal.

$$PE^* = \text{Max}_i \{Q(M_i)\}$$

Where Q(.) is a quality function that can be defined for any type of measurement signal. The best pupil entry location is the one that gives the highest or maximum A-scan quality signal. A processor would evaluate the quality function for a plurality of measurement data and determine the optimal pupil entry location. In the example shown in FIG. 7, the optimum position, is indicated with an arrow 702. In the case of UV-A, the optimum pupil entry position is irrelevant as the measurements do not progress beyond the pupil. In the case of UV-I and UV-P, the degradation introduced by the crystalline lens will need to be evaluated by locating the pupil entry point that produces the minimum signal attenuation from the crystalline lens. First, the haze/flare of the anterior segment can be determined that does not involve measurements downstream of it. Second, intensities of A-scans can be obtained downstream of the anterior segment, and covering a grid of entry points as outlined above, in order to determine the optimum value for the quality function. The A-scan with the optimum value of the quality function can then be used to estimate the best entry point for acquisition. A-Scans obtained through the chosen entry point can then be used to evaluate haze/flare.

The framework for avoiding the effect of lens opacities on the uveitis grading is general and hence can be used for any type of measurement signal. For example, if the measurement system is an FD-OCT system, each measurement signal will be an A-scan or B-scan. For an OCT system with an A-scan as the measurement signal, the quality function may be defined as the Signal to Noise Ratio (SNR).

$$Q(M_i) = SNR(M_i)$$

The SNR may be calculated based on a very rough segregation of the signal from the A-scan into signal and noise components. The SNR can be defined as:

$$SNR(M_i) = \frac{\text{Mean}(M_i^{signal})}{\sigma(M_i^{noise})}$$

Where Mean( ) function is the averaging function, $M_i^{signal}$ is the useful data in the measurement signal and $M_i^{noise}$ is the noise part of the measurement signal. $\sigma(M_i^{noise})$ is the standard deviation of the noise.

Once the optimal pupil entry position is determined, a controller can direct the measurement system to acquire image data at the desired pupil entry position. Pupil tracking can then be engaged to track the position of the pupil and hence maintain the pupil entry location at the optimal location. This position can be maintained for a single measurement session, throughout a single visit, or can be recalled for precise positioning of the measurement beam on repeat or follow-up visits. This allows for precise monitoring of changes in levels of inflammation due to disease progression or due to treatments.

While the methods described are focused on selecting a specific measurement beam location, such as 702 in FIG. 7, based on a quality of the measurement data, the basic concepts can be generalized to maintain any measurement beam location over time or multiple visits. This could be the center of the pupil or a location on the pupil selected by the user. Furthermore, the system could check to insure that the user selected point lies within the boundaries of the pupil in order to reduce vignetting that will occur if the beam width is partially or entirely blocked by the iris.

Any of the methods presented in the present application can be programmed to operate on a generic computer; placed onto a computer readable medium or via a physical carrier signal to a computer encoded with a computer program to execute said methods.

The following references are hereby incorporated by reference:

PATENT REFERENCES

U.S. Pat. No. 6,095,648
U.S. Pat. No. 7,805,009
U.S. Pat. No. 8,348,429
U.S. Pat. No. 8,632,180
US Patent Publication No. 2009/0244485
US Patent Publication No. 2007/0291277
US Patent Publication No. 2012/0249956
US Patent Publication No. 2012/0274897
US Patent Publication No. 2014/0276025
US Patent Publication No. 2015/0062590
PCT Publication No. WO2013/148687

NON-PATENT REFERENCES

Agarwal et al. (2009), Am J Ophthal 147(3), 413-416
Agarwal et al. (2008), Ophthalmology Times Europe 4(2).
Davis et al. (2010), Am J Ophthal 150(5), 637-641.
Davis, J. L. (2012), PA073, presentation at AAO 2012 (Chicago).
Madow et al. (2011), Am J Ophthal 152(2), 170-176.
Kaufman and Rousseeuw (2005), *Finding Groups in Data: An Introduction to Cluster Analysis*, Wiley.
Lowder et al. (2004), IOVS, 45 E-abstract 3372.
Lee et al. (2006), Opt Exp 14(10), 4403.
Kim et al. (2010), Expert Rev. Ophthalmol. 5(5), 699-713.
Ai et al. (2006), in Intell Control & Automation, WCICA 2006, 9799-9803.
Huang et al. (1991), Science 254, 1178-1181.

The invention claimed is:

1. A method for automatically analyzing images of an eye of a patient in order to grade the level of opacity associated with proteins in the anterior and/or posterior chambers of the eye, comprising:
    collecting image data of the eye of the patient with an imaging device, said imaging device including a light source, a detector for measuring light returned from the eye and a processor for analyzing the returned detected light;
    identifying and extracting characteristic metrics from the image data associated with the opacity of the eye, said characteristic metrics including one or more of gradient and texture;
    comparing the identified and extracted characteristic metrics with characteristic metrics derived from a set of images of eyes from a population of subjects to grade the level of opacity of the collected image data;
    determining the level of opacity in the lens of the eye;
    adjusting the determined grade level of opacity based on the level of opacity in the lens; and
    displaying the adjusted grade on a display or storing the adjusted grade in the processor.

2. A method as recited in claim 1, in which the comparing step is carried out by a machine learning classifier.

3. A method as recited in claim 2, in which the machine learning classifier is of the supervised type.

4. A method as recited in claim 1, in which the image data is collected using an optical coherence tomography (OCT) system.

5. A method as recited in claim 1, in which the image data is collected using a fundus imaging system.

6. A method as recited in claim 4, further comprising identifying cell clumps in the OCT image data and using the identified cell clumps and the determined opacity grade to grade the overall level of inflammation in the eye or part of the eye.

7. A method as recited in claim 1, further comprising dividing the image data into subsections and identifying and extracting characteristics related to opacity with the subsections of image data.

8. A method as recited in claim 1, in which the image data is collected at a pupil entry point selected to minimize the impact of lens opacities in the image data.

9. A method for automatically analyzing images of an eye of a patient in order to grade the level of opacity associated with proteins in the anterior and/or posterior chambers of the eye, comprising:

collecting image data of the eye of the patient with an imaging device, said imaging device including a light source, a detector for measuring light returned from the eye and a processor for analyzing the returned detected light;

dividing the image data into subsections;

identifying and extracting characteristic metrics from the image data associated with the opacity of the eye within the subsections, said characteristic metrics including one or more of intensity, contrast, gradient and texture;

comparing the identified and extracted characteristic metrics with characteristic metrics derived from a set of images of eyes from a population of subjects to grade the level of opacity of the collected image data;

determining the level of opacity in the lens of the eye;

adjusting the determined grade level of opacity based on the level of opacity in the lens; and displaying the adjusted grade on a display or storing the adjusted grade in the processor.

10. A method as recited in claim 9, in which the comparing step is carried out by a machine learning classifier.

11. A method as recited in claim 10, in which the machine learning classifier is of the supervised type.

12. A method as recited in claim 9, in which the image data is collected using an optical coherence tomography (OCT) system.

13. A method as recited in claim 9, in which the image data is collected using a fundus imaging system.

14. A method as recited in claim 12, further comprising identifying cell clumps in the OCT image data and using the identified cell clumps and the determined opacity grade to grade the overall level of inflammation in the eye or part of the eye.

15. A method as recited in claim 9, in which the image data is collected at a pupil entry point selected to minimize the impact of lens opacities in the image data.

* * * * *

UNITED STATES PATENT AND TRADEMARK OFFICE
CERTIFICATE OF CORRECTION

PATENT NO. : 10,149,610 B2
APPLICATION NO. : 14/688753
DATED : December 11, 2018
INVENTOR(S) : Harihar Narasimha-Iyer et al.

It is certified that error appears in the above-identified patent and that said Letters Patent is hereby corrected as shown below:

In the Specification

Column 3, Line 50, delete "a the" and insert -- the --, therefor.

Column 3, Lines 59-60, delete "and or" and insert -- and/or --, therefor.

Column 9, Line 46, delete "Rousseuw" and insert -- Rousseeuw --, therefor.

Signed and Sealed this
Sixteenth Day of July, 2019

Andrei Iancu
*Director of the United States Patent and Trademark Office*